United States Patent [19]

Hedrick

[11] 4,131,116

[45] Dec. 26, 1978

[54] ROTARY BONE CUTTER FOR SHAPING SOCKETS

[75] Inventor: John R. Hedrick, La Crescenta, Calif.

[73] Assignee: Pevrick Engineering Company, Inc., Sun Valley, Calif.

[21] Appl. No.: 792,935

[22] Filed: May 2, 1977

[51] Int. Cl.² ........................ A61B 17/32; A61B 17/18
[52] U.S. Cl. ................................... 128/305; 128/92 E; 30/279 R; 408/207; 408/226; 408/227
[58] Field of Search ........................ 128/92 E, 83, 305; 408/204, 207, 226, 227; 30/279 R, 124; 407/30, 53, 54, 62

[56] References Cited

U.S. PATENT DOCUMENTS

| 1,916,874 | 7/1933 | Wilhelm | 407/54 X |
| 3,633,583 | 1/1972 | Fishbein | 128/305 |
| 3,702,611 | 11/1972 | Fishbein | 128/305 |
| 4,023,572 | 5/1977 | Weigand et al. | 128/305 |

FOREIGN PATENT DOCUMENTS 2233972  1/1975  France ..................... 128/92 E

Primary Examiner—Ronald L. Frinks
Attorney, Agent, or Firm—Richard J. Rodrick

[57] ABSTRACT

A bone cutter for shaping a socket, such as a hip socket, comprising a cutter head located at one end of a rotatably driven shaft and having a hemispherical portion with a hemispherical exterior surface, the hemispherical portion containing a closed hollow chamber, and openings, such as slots, in said hemispherical portion connecting between the exterior surface and the chamber, the trailing portion of each of the openings having a cutting edge raised slightly above the hemispherical surface to move material from the socket into the chamber during rotation of the cutter head, and quick release means for connecting and disconnecting the cutter head and the shaft.

8 Claims, 8 Drawing Figures

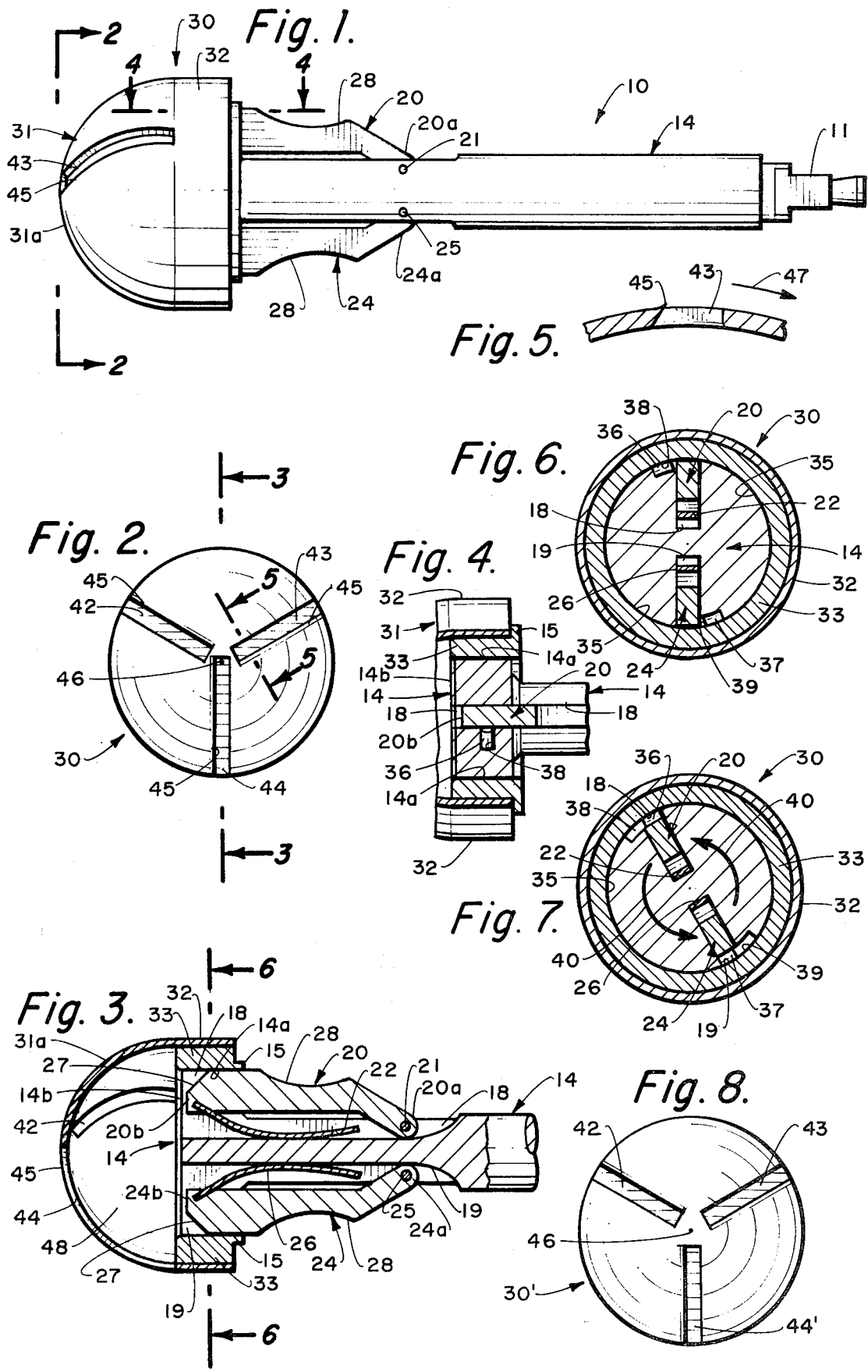

ROTARY BONE CUTTER FOR SHAPING SOCKETS

BACKGROUND OF THE INVENTION

Power driven reamers or bone cutters are utilized to round out and reshape the cavity or socket of the hip, following the destruction of cartilage or bone at the hip socket. Such power driven bone cutters utilize a plurality of blades having the cutting edges projecting slightly from the rotary hemispherical head of the cutter. In U.S. Pat. No. 3,633,583 to Meyer Fishbein granted Jan. 11, 1972, there is shown a substantially hemispherical head in which a single surgical blade is so shaped as to provide two radially disposed cutting edges on opposite sides of the rotational center line of the head. The edges project just slightly above the adjustment substantially hemispherical surface of the cutting head and the cutting edges are beveled in opposite directions on opposide sides of the axis of rotation so that both edges will cut during rotation of the head. Troughs or grooves are formed in the head forward of the cutting edges to transport the cut material from the surface of the head to the back end of the head. Thus, loose cut material can be present at the site of the cutting operation. Further, in this prior device, the manner in which the cutter head is attached to the drive shaft does not make it possible to quickly change the cutter head. In some cutting operations, more than one size of hemispherical cutter head must be utilized to obtain the necessary change in dimension of the socket, particularly in the case where a plastic sleeve is to be added to the socket, and quick changing of the cutter heads is desirable in this case. Also, since the cutting edges of the prior device are 180° apart, there is less resistance to tipping of the rotating axis of the cutter head than if more blades were utilized.

SUMMARY OF THE INVENTION

The bone cutter of this invention has a substantially hemispherical shaped cutter head with a plurality of radial cutter slots passing from the exterior surface of the cutter head into a hollow chamber within the head. At the trailing side of each slot is formed a cutting edge which projects slightly above the surface of the cutter head. Each cutter edge extending beyond the surface of the head removes a small portion of bone or cartilage from the hip socket and this bone passes through the slot forward of the cutting edge into the head chamber where it is retained until the head is removed from the drive shaft. Thus, there is no loose bone or cartilage in the vicinity of the hip socket during rotation of the cutter head. By using at least three slots and cutting edges, the head is equally loaded during rotation in all radial directions so that there is no tendency for tipping of the axis of rotation of the head as the cutting operation proceeds. The cutting edges and slots are so formed in the head that at least one slot and cutting edge passes over the point at which the end of the axis of rotation intersects the cutter head so that the complete surface of the hip socket is removed. However, in cases where it is desired to leave a flat portion at the bottom of the socket, all of the slots and cutting edges will terminate short of the point at which the axis of rotation intersects the head.

The connection between the rotating shaft and the cutter head can be easily operated to quickly connect and disconnect the cutting head. The open end of the cutter head contains an attachment ring having two inwardly extending pins and each pin passes through a groove in an enlarged flange on the end of the rotary shaft. A cavity in the flange connects with each groove so that each pin can be located in a cavity upon rotation of the cutting head relative to the enlarged flange. Pivotally mounted locking members are located in the grooves in the flange and move outwardly to cover the cavities and confine the pins in order to attach the cutting head to the rotating shaft. The head can be easily removed from the flange by manually moving the locking members inwardly in the grooves and rotating the head so that the pins move out of the cavities and upwardly out of the groove. The thickness of the attachment ring can be varied so that the ring can mount cutter heads of varying hemispherical radius. Thus, the size of the head can be progressively increased to progressively enlarge a given socket while using the same drive shaft. Also, since it is easy to remove the head, the cut bone can be readily taken out of the chamber in the cutter head and the head can then be quickly replaced for further cutting. Thus, there is no danger that the cut material will interfere with the cutting operation in any way because the cut material is completely confined during rotation of the head within the chamber in the head.

The present invention therefore provides a bone cutter having a cutting head containing slots and cutting edges which move the scrapings and bone cuttings into a normally closed chamber in the cutter head during rotation of the head, and the cuttings cannot escape into the operating area until such time as the power drive is stopped and the head is removed for cleaning. Further, by the use of at least three cutting blades, the maintenance of the axis of cutting is more easily assured and by providing a quick disconnect of the cutter head from the drive shaft, it is possible to easily change the size of the cutter head to enlarge the size of the hip socket.

BRIEF DESCRIPTION OF THE DRAWING

FIG. 1 is a side elevational view of the rotary bone cutter of the present invention showing the rotating head connected to a rotary drive shaft;

FIG. 2 is an end elevational view along line 2—2 of FIG. 1 illustrating the slots in the cutter head;

FIG. 3 is a vertical section along line 3—3 of FIG. 2 illustrating the locking mechanism for attachment of the cutter head to the drive shaft and showing the chamber in the cutter head;

FIG. 4 is a horizontal section, partly in elevation, along line 4-4 of FIG. 1 showing a locking arm in a groove in the enlarged flange at the end of the drive shaft;

FIG. 5 is an enlarged transverse section across one of the slots in the cutter head showing the raised cutting edge at the trailing side of the slot;

FIG. 6 is a transverse vertical section along line 6—6 of FIG. 3 illustrating the locking arms in locked position;

FIG. 7 is a sectional view similar to FIG. 6 with the locking arms moved inwardly to the unlocking position; and FIG. 8 is an end elevational view similar to FIG. 2 of a modified cutting head in which the slots and cutting edges do not extend to the point of intersection of the axis of rotation with the surface of the cutter head.

DETAILED DESCRIPTION OF THE PREFERRED EMBODIMENT

Referring to FIG. 1, driving shaft 10 has end 11 on which the surfaces are shaped to be connected to a rotary power device (not shown). It is understood that any suitable connection between shaft 10 and a power device can be utilized to rotate the shaft and the connection forms no part of the present invention. Upon connection of the end 11 to the power drive, the shaft 10 is rotated during operation of the power drive. The other end of the shaft 10 comprises an enlarged cylindrical flange 14 (See FIG. 4) which has a rim 15 extending from the outer surface 14a of the flange. Radial grooves 18 and 19 are cut at opposide locations in the circumference of the shaft 10 and extend axially through the enlarged flange 14. The grooves are of substantially uniform depth in the shaft and continue straight through the circumference of flange 14 to the end surface 14b of the flange, as illustrated in FIG. 3.

A locking arm 20 is located at groove 18 and one end 20a projects into the groove for pivotal connection to the shaft 10 by a pin 21. A spring 22 is connected to the other end 20b of the locking arm and the body of the spring 22 is located in the groove 18 so as to normally bias the arm 20 outwardly. In a similar manner, locking arm 24 is located at groove 19 and is pivotally mounted to shaft 10 at one end 24a by a pin 25. A spring 26 is connected to the other end 24b of locking arm 24 and resides in the groove 19 in order to bias the arm 24 outwardly. As illustrated in FIG. 3, the ends of the locking arms to which the springs are attached, reside in the portion of the grooves 18 and 19 located within the flange 14. Each locking arm is provided with a finger recess 28 so that the arms can be pushed together by gripping these surfaces with the fingers, as illustrated in FIG. 7.

A cutter head 30 has a hemispherical portion 31 and a cylindrical portion 32 coextensive with the portion 31. The cylindrical portion 32 contains a solid ring 33 attached thereto and the interior diameter of ring 33 is such that the ring fits snugly over the outer surface 14a of the flange 14 and slides up against the lip 15. Two locking pins 36 and 37 extend from opposite sides of the interior surface 35 of ring 33 (see FIGS. 6 and 7).

The grooves 18 and 19 in the flange 14 have on one side thereof cavities 38 and 39, respectively. The ring 33 can be moved over flange 14 when pins 36 and 37 are located to move into grooves 18 and 19, respectively. The locking arms 20 and 24 are squeezed together so that the pins can pass into the grooves 18 and 19 and become located opposite the cavities 38 and 39 (See FIG. 7). With the ring 33 engaging the lip 15 relative rotation between the cutter head 30 and the enlarged flange 14, in the direction of arrows 40 in FIG. 7, will cause pins 36 and 37 to enter cavities 38 and 39, respectively. Thereafter, release of the locking arms will cause springs 22 and 26 to move the ends of the locking arms outwardly against ring 33 and the ends of the arm will lock the pins in the cavities, (See FIGS. 3 and 6). Ends 20b and 24b of the arms each have a slanted surface portion 27 which is engaged by a locking pin as the pins move downward in the grooves and movement of the pins move the locking arms inwardly into the grooves to permit the pins to become opposite the cavities 38 and 39. Thus, the inward movement of the locking arms is facilitated both by the finger recesses 28 on the arms and by the slanted surfaces 27. After the pins 36 and 37 are locked by the locking arms in the cavities 38 and 39, respectively, rotation of the shaft 10 will cause rotation of the enlarged flange 14 and this rotation will be imparted by the pins 36 and 37 to the cutter head 30. In the locking position, the pins are snugly within the cavities 38 and 39 so that there is no substantial clearance in the drive motion. It is apparent that the radial width of the ends 20b and 24b of the locking arms is less than the depth of grooves 18 and 19, respectively, in the flange 14 so that when the arms are squeezed inwardly, the ends clear the cavities 38 and 39 so that the pins can move through the grooves and into the cavities. Also, during rotation of the head the ends of the locking arms are forced outwardly by centrifugal force against the ring 33 in order to retain the position which holds the pins in the cavities. The spring 22 and 26 exert sufficient outward force to hold the pins in the grooves and lock the cutter head to the shaft when it is not rotating.

Referring to FIGS. 1 and 2, the hemispherical portion 31 has a hemispherical exterior surface 31a and contains a plurality of openings, each having a cutting edge on its trailing portion. Preferably, portion 31 contains three open slots 42, 43 and 44 (See FIG. 2) which are located in radial planes of said hemispherical portion at 120° intervals around the head. As illustrated in FIG. 5, each of the slots has a cutting edge 45 at the trailing side which is raised slightly above the hemispherical surface of the hemispherical portion and is pointed in the direction of rotation of the cutter head as indicated by arrow 47 in FIG. 5. As illustrated in FIG. 2, slots 42 and 43 stop short of the point 46 at which the axis of rotation intersects the hemispherical portion 31, whereas the slot 44 extends past the point 46 so that cutting edge 45 of slot 44 will remove the bottom of the cavity. Thus, the three cutting edges 45 combined will cut the entire hemispherical surface of the bone socket.

The bone cuttings and scrapings from each of the cutting edges 45 move inwardly from the hemispherical surface through the slots on which the cutting edges are formed and into hollow chamber 48 within the hemispherical portion 31. The end surface 14b of the flange 14, the ends 20b and 24b of the locking arms and the springs 22 and 26 serve to substantially close the hollow chamber when the cutter head 30 is attached to the shaft. Thus, the substantially closed chamber 48 will retain the cuttings and scrapings developed by the rotation of the cutting edge 45 so that this material will not interfere with the cutting operation or with access to the surrounding area. When it is desired to clean the cutting head of this material, it is only necessary to grip the recess 28 of the locking arms and move the arms inwardly so that the cutting head can be easily removed and cleaned out and thereafter reattached to the rotating shaft 10. By utilizing at least three cutting edges equally spaced apart, there are three equally spaced lines of cutting pressure on the hemispherical head and there is no tendency for the head to tip one way or the other.

In operation of the device on a hip socket, it may be necessary to start with a cutting head of smaller radius and increase the size of the cutter head in increments to substantially enlarge the radius of the socket. The size of the cutter head used on a given enlarged flange 14 can be decreased or increased by using different radial thicknesses of ring 33. A larger radius head would have a thicker ring 33 than would a smaller radius head out both could be used on the same size of flange 14. It is understood that while the ring 33 is illustrated as being separate from the cylindrical surface portion 32, it could be made integral therewith. Of course, the size of flange 14 can be varied to support different size ranges of cutter heads. Additional cutting slots could be placed in the hemispherical portion 31, each with its own cutting edge 45. A modified cutter head 30' is shown in FIG. 8 and contains slots 42 and 43 and a slot 44' of reduced length so that the slot and cutting edge does not reach to point 46. In using this head, material will not be removed from the very bottom of the socket.

The present invention provides a quick attachment between the drive shaft and the cutter head to permit easy replacement and removal of the cutter head and the attachment results in a substantially closed cavity being formed in the cutter head to receive the bone cuttings so that they will not interfere with the operation and cutting operation. It is understood that the ends of the springs 22 and 26 in grooves 18 and 19, respectively, can be slidably attached to shaft 10 in some suitable manner so that the ends will not fall out of the grooves and the outward movement of the locking arms would be limited. Other suitable means could be utilized for attachment of the cutter head. Also, it is understood that the cutting edges 45 could be formed by simply forging one edge of each slot outwardly above the hemispherical surface and thereafter sharpening the edge rather than by forming the cutting edge from a separate piece of material which must be attached to the trailing side of the slot.

What is claimed is:

1. A bone cutter for shaping a socket comprising:
a shaft adapted to be selectively rotated at one end;
a cutter head comprising a hemispherical portion having a hemispherical exterior surface and containing a hollow chamber;
means located at the opposite end of said shaft for connecting said hemispherical portion to the opposite end of said shaft and for closing said chamber;
at least three elongate slots in a radial plane of said hemispherical portion connecting between said hemispherical exterior surface and said chamber, said slots coverging toward the center point of said hemispherical exterior surface but being unconnected to each other at said point; and
a cutting edge on the trailing portion of each of said slots and raised slightly above said hemispherical exterior surface of said hemispherical portion for moving material from said socket into said chamber during rotation of said shaft.

2. A bone cutter for shaping a socket comprising:
a shaft adapted to be selectively rotated at one end;
a cutter head comprising a substantially hemispherical portion having a hemispherical exterior surface and a cylindrical portion extending from the end of said hemispherical portion;
means for releasably connecting said cylindrical portion of said cutter head to the other end of said shaft;
a hollow chamber within said hemispherical portion substantially closed by said other end of said shaft and said connecting means;
at least three elongate slots in a radial plane of said hemispherical portion connecting between said hemispherical surface and said chamber, said slots converging toward the center point of said hemispherical exterior surface but being unconnected to each other at said point; and
a cutting edge located along the trailing side of each of said slots and extending slightly outwardly from said exterior hemispherical surface of said hemispherical portion for moving material from said socket into said chamber during rotation of said shaft.

3. A bone cutter as defined in claim 2:
said slots being three in number and located in radial planes spaced one hundred and twenty degrees apart.

4. A bone cutter as defined in claim 3:
one of said slots extending across the point of intersection of the rotating axis of said shaft with said hemispherical portion, the cutting edge on said one slot adapted to remove the bottom of said socket upon rotation of said cutter head.

5. A bone cutter for shaping a socket comprising:
a shaft adapted to be selectively rotated at one end;
a cutter head comprising a substantially hemispherical portion having a hemispherical exterior surface and a cylindrical portion extending from the end of said hemispherical portion;
means for releasably connecting said cylindrical portion of said cutter head to the other end of said shaft,
said releasably connecting means comprising an enlarged cylindrical flange on said other end of said shaft having an exterior cylindrical surface;
a plurality of radial grooves in the circumference of said flange;
a cavity in one side of each of said grooves;
said cylindrical portion of said cutter head having an inside surface fitting snugly over said exterior cylindrical surface of said flange, said inside surface having a plurality of pins extending therefrom, each pin being movable in one of said grooves by axial movement of said head relative to said shaft and thereafter movable into one of said cavities by relative rotation between said head and said shaft;
means for locking said pins in said cavities during operation of said shaft in order to rotate said cutter head;
a hollow chamber within said hemispherical portion substantially closed by said other end of said shaft and said connecting means;
a plurality of openings in said hemispherical portion connecting between said hemispherical surface and said chamber; and
a cutting edge located along the trailing side of each of said openings and extending slightly outwardly from said exterior hemispherical surface of said hemispherical portion for moving material from said socket into said chamber during rotation of said shaft.

6. The bone cutter as defined in claim 5:
said locking means comprising a plurality of locking arms each pivotally mounted to said shaft at one end, the other end of each locking arm being movable in one of said grooves in said flange, said other ends of said arms in their inward position clearing said cavities to permit movement of said pins through said grooves and rotation into said cavities, said other ends being biased outwardly against said cylindrical portion to retain said pins in said cavities.

7. A bone cutter as defined in claim 5:
said grooves, cavities and pins being two in number and said grooves being opposite one another.

8. A bone cutter as defined in claim 6:
a spring connected to each of said locking arms and acting against said shaft for biasing each of said other ends of said locking arms outwardly.

* * * * *